(12) United States Patent
Isenburg

(10) Patent No.: US 12,138,365 B1
(45) Date of Patent: *Nov. 12, 2024

(54) DRY INFLATED DECELLULARIZED EXTRACELLULAR MATRIX

(71) Applicant: Reprise Biomedical, Inc., Plymouth, MN (US)

(72) Inventor: Jason Isenburg, Plymouth, MN (US)

(73) Assignee: Reprise Biomedical, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/834,561

(22) Filed: Jun. 7, 2022

Related U.S. Application Data

(60) Provisional application No. 63/208,596, filed on Jun. 9, 2021.

(51) Int. Cl.
| | |
|---|---|
| *A61L 27/36* | (2006.01) |
| *A61L 27/38* | (2006.01) |
| *A61L 27/54* | (2006.01) |
| *A61P 17/02* | (2006.01) |

(52) U.S. Cl.
CPC ....... *A61L 27/3683* (2013.01); *A61L 27/3839* (2013.01); *A61L 27/54* (2013.01); *A61P 17/02* (2018.01)

(58) Field of Classification Search
None
See application file for complete search history.

(56) References Cited

U.S. PATENT DOCUMENTS

| | | | |
|---|---|---|---|
| 9,974,814 | B2 | 5/2018 | Katane et al. |
| 11,602,548 | B1 * | 3/2023 | Klitzke ................. A61K 35/51 |
| 11,998,662 | B1 | 6/2024 | Isenburg et al. |
| 2005/0266390 | A1 * | 12/2005 | Ueda ....................... A61F 2/062 623/925 |
| 2016/0279170 | A1 * | 9/2016 | Katane ................ A61L 27/3683 |

OTHER PUBLICATIONS

Mattei, G., et al., Artificial Organs 41(12); E347-E355 (2017). (Year: 2017).*
"U.S. Appl. No. 18/448,259, Examination Report mailed Feb. 29, 2024," 26 pgs.
Mostow, E., et al. "Effectiveness of an extracellular matrix graft (OASIS Wound Matrix) in the treatment of chronic leg ulcers; A randomized clinical trial," J Vasc Surg 41: 837-843 (2005).
"U.S. Appl. No. 18/448,250, Examination Report mailed Nov. 27, 2023," 27 pgs.
Silvestry-Rodriguez, Nadia, et al. "Silver as a Disinfectant," Rev Environ Contam Toxicol 191:23-45 (2007).
"U.S. Appl. No. 18/448,259, response to first Examination Report, filed Mar. 6, 2024" 8 pgs.
"U.S. Appl. No. 18/448,250, Response to Examination Report, filed Feb. 27, 2024," 13 pgs.
"U.S. Appl. No. 18/448,250, Response to 2nd Office Action, filed Aug. 22, 2024," 20 pgs.
"U.S. Appl. No. 18/624,746, Response to 1st Office Action filed Aug. 12, 2024," 9 pgs.
"U.S. Appl. No. 18/448,250, final rejection mailed Apr. 24, 2024," 27 pgs.
"U.S. Appl. No. 18/624,746, Office Action mailed May 31, 2024," 27 pgs.

* cited by examiner

*Primary Examiner* — David J Blanchard
*Assistant Examiner* — Daniel F Coughlin
(74) *Attorney, Agent, or Firm* — Gregory W. Smock

(57) ABSTRACT

An inflated and suspension dried decellularized extracellular matrix of a mammalian organ or tissue, or a vascularized portion thereof, and methods of making and using the inflated and suspension dried material, are provided.

18 Claims, 5 Drawing Sheets

DRY INFLATED DECELLULARIZED EXTRACELLULAR MATRIX

CROSS-REFERENCE TO RELATED APPLICATIONS

This application claims the benefit of the filing date of U.S. application No. 63/208,596, filed on Jun. 9, 2021, the disclosure of which is incorporated by reference herein.

BACKGROUND

The extracellular matrix (ECM) is a complex network of structural and functional proteins that form tissue-specific architectures. The ECM includes secreted products of resident cells in each tissue and organ. The matrix molecules include structural and functional proteins, glycoproteins, and glycosaminoglycans. The resident cells of the ECM, besides producing ECM, receive signals therefrom, allowing for tissue development and/or homeostasis. Those properties are the basis for the use of ECM-based materials in tissue engineering and regenerative medicine. Because ECM provides a naturally occurring and highly conserved substrate for cell viability and growth that has reduced immunogenicity, ECM-based substrates having individual ECM components or of whole decellularized tissues have been used in a wide range of applications in both preclinical and clinical settings.

SUMMARY

The disclosure provides an inflated and suspension dried decellularized extracellular matrix of a mammalian organ or tissue, or a vascularized portion thereof, e.g., a portion that is greater than about 8 $cm^3$, e.g., greater than about 12 $cm^3$ or greater than about 16 $cm^3$, wherein said decellularized extracellular matrix of a mammalian organ or tissue or portion thereof comprises a decellularized vascular tree, duct or cavity, wherein said decellularized extracellular matrix including the vascular tree retains the morphology of said extracellular matrix prior to decellularization, wherein when fluid or a gas is introduced to one entry point in said vascular tree of said decellularized extracellular matrix, said fluid is retained in the vascular tree so that the fluid or gas exits through a different route of the vascular tree, and wherein said portion optionally does not include an exterior surface. In one embodiment, the mammalian organ is a heart, a kidney, a liver, spleen, pancreas, bladder, skeletal muscle, small bowel, large bowel, stomach, bone, brain, or a lung. In one embodiment, the vascularized portion is a portion of a mammalian heart, a kidney, a liver, spleen, pancreas, bladder, skeletal muscle, small bowel, large bowel, stomach, bone, brain, or a lung. In one embodiment, the inflated and suspension dried decellularized extracellular matrix is inflated and dried with air, oxygen or nitrogen. In one embodiment, the inflated and suspension dried decellularized extracellular matrix has an exterior surface or portion thereof. In one embodiment, the inflated and suspension dried decellularized extracellular matrix does not have an exterior surface or portion thereof. In one embodiment, the inflated and suspension dried decellularized extracellular matrix has a thickness of about 1 cm to 2 cm, 1.5 cm to 2.5 cm or 2 cm to 3 cm. In one embodiment, the inflated and suspension dried decellularized extracellular matrix is compressed. In one embodiment, the inflated and suspension dried decellularized extracellular matrix has and retains a height that is increased by at least 25% relative to a corresponding uninflated and/or nonsuspension dried decellularized extracellular matrix of the mammalian organ or tissue, or portion thereof. In one embodiment, the inflated and suspension dried decellularized extracellular matrix comprises multiple stacked layers of the portion. In one embodiment, the portion is about 2 cm (L)×2 cm (W)×2 cm (T), 3 cm (L)×3 cm (W)×2 cm (T), 5 cm (L)×5 cm (W)×2 cm (T), or 10 cm (L)×10 cm (W)×2 cm (T). In one embodiment, the decellularized organ or vascularized tissue is a pig, bovine, sheep, canine or human. In one embodiment, a dry decellularized extracellular matrix of a mammalian organ or tissue, or a vascularized portion thereof prepared by the methods disclosed herein has a moisture content of about 4% to about 7.5%, e.g., about 4.6% to about 6.1%. In one embodiment, the moisture content is no more than 8% or no more than 7.5%.

Also provided is an ex vivo method of inflating and suspension drying a decellularized extracellular matrix of a mammalian organ or tissue, or a vascularized portion thereof. The method includes providing a suspended decellularized extracellular matrix of a mammalian organ or tissue, or portion thereof, wherein said extracellular matrix of said organ optionally comprises an exterior surface, wherein said extracellular matrix of said organ or tissue, or portion thereof, comprises a vascular tree, wherein said decellularized extracellular matrix of said organ or tissue or portion thereof retains a majority of fluid or gas introduced to the decellularized extracellular matrix vascular tree, and wherein said organ has a substantially closed vasculature bed; cannulating said organ or tissue, or portion thereof, at one or more vessels, cavities and/or ducts, thereby producing a cannulated organ or portion thereof or a cannulated tissue or portion thereof; and introducing a gas into said one or more vessels, cavities or ducts of said cannulated organ or portion thereof, for at least four hours so as to provide an inflated and suspension dried extracellular matrix. In one embodiment, the gas is introduced for up to 96 hours. In one embodiment, the gas is introduced for up to 72 hours. In one embodiment, the gas is introduced at a maximum rate of 4000 mL/min. In one embodiment, the inflated decellularized extracellular matrix has and retains a height that is increased by at least 25% relative to a corresponding uninflated decellularized extracellular matrix of the mammalian organ or tissue, or portion thereof. In one embodiment, the gas comprises air, nitrogen or oxygen. In one embodiment, the mammal is a human, non-human primate, bovine, porcine, canine, feline, caprine, ovine, or rodent. In one embodiment, the method further includes dividing (separating, e.g., via cutting) the inflated and suspension dried extracellular matrix into one or more portions greater than about 0.5 cm (L)×0.5 cm (W)×0.5 cm (T). In one embodiment, the method further includes removing the exterior surface, e.g., before or after gas introduction. In one embodiment, the method further includes removing the exterior surface after inflation and suspension drying. In one embodiment, the method further includes sterilizing the inflated and suspension dried decellularized extracellular matrix. In one embodiment, the mammalian organ is a heart, a kidney, a liver, spleen, pancreas, bladder, skeletal muscle, small bowel, large bowel, stomach, bone, brain, or a lung.

Further provided is a portion of an inflated and suspension dried decellularized extracellular matrix of a mammalian organ or tissue, e.g., produced by the method disclosed herein. In one embodiment, the portion is compressed. In one embodiment, the portion forms part of a product having layers of portions. In one embodiment, the portion or a plurality of portions is/are morselized or granularized. In one embodiment, the portion or a plurality of portions is/are milled, e.g., in a blender, to produce fragments in a range of sizes. In one embodiment, the milled product has a population of molecules having a particle length from approximately 0.01 mm to about 40 mm, e.g., about 0.1 mm to about 20 mm. In one embodiment, the milled product has a population of molecules having a particle length that is greater than 0.04 mm. In one embodiment, the milled product has a population of molecules having a particle length that is greater than 0.4 mm. The milled product may be placed, or shaped and then placed, into irregularly shaped wound beds and crevices, while providing considerably more bulk than traditional powder products. The fibers may be packaged in a container such as a plastic tray with lid, or alternatively, in a glass vial or bottle. In one embodiment, the container includes about 100 mg, 500 mg, or 1000 mg (by particle weight). The product is sterilized, e.g., by electron beam (e-beam) irradiation, for instance, at 25 to 35 kGy. The product may be applied dry or wetted in an appropriate solution, such as physiological saline or lactated Ringer's solution, before application to a wound.

In one embodiment, a method to augment a void or treat a wound in a body cavity, or to treat a topical wound, of a mammal is provided that includes administering to the void or the wound, a portion of extracellular matrix disclosed herein. In one embodiment, the administration is to a fistula. In one embodiment, the administration is to a hernia.

In one embodiment, a package comprising a product comprising the portion of the extracellular matrix is provided. In one embodiment, the product comprises two or more layers of the portion.

Further provided is a method to prepare a gas filled (inflated), dried decellularized extracellular matrix of a mammalian organ or vascularized portion thereof, or a vascularized mammalian tissue or a portion thereof. In one embodiment, the three dimensional decellularized extracellular matrix retains the shape of the original organ or portion thereof, or tissue or portion thereof. In one embodiment, the extracellular matrix after inflation has a height that is greater than about 2 cm up to about 6 cm, e.g., about 2 cm to about 5 cm, including about 2 cm to about 4 cm, relative to that of a corresponding uninflated extracellular matrix. For example, the extracellular matrix of a liver lobe of a large mammal after inflation has a height that is greater than about 3 cm to about 5 cm, including about 4 cm, relative to that of a corresponding uninflated extracellular matrix of a liver lobe. In one embodiment, the extracellular matrix after inflation and drying has a height that is increased by at least 25% up to 1000%, e.g., at least 50% up to about 500% or about 75% up to about 250%, relative to a corresponding uninflated extracellular matrix. In one embodiment, the gas filled, dried decellularized extracellular matrix of an organ or tissue has a shape, size or volume that is about 25% to 125%, for example, about 50% to about 150% or about 75% to about 110%, that of the corresponding native organ or tissue. The active introduction of a gas, for instance a vapor (a gas having particles or droplets), into a decellularized extracellular matrix of an organ or tissue via its natural vasculature or any other conduit, e.g., duct or cavity, provides for a gas filled decellularized extracellular matrix of an organ or tissue matrix that is expanded relative to its non-inflated shape, and in some embodiments has the original shape of the native (cellularized) organ or tissue prior to decellularization. The shape of the gas filled decellularized extracellular matrix, for example one filled with air, is retained as a result of the gas being trapped within the tissue or organ and filling the spaces originally occupied by cells.

In one embodiment, the gas is retained in the extracellular matrix in the absence of a seal. The product is a three dimensional decellularized extracellular matrix that can be used for but is not limited to implantation as surgical mesh, surgical filler, void fillers, tissue engineering, and the like. Inflation allows the matrix to open up by filling the compartments where cells used to occupy, thus allowing for the matrix to be easily cut because it becomes more rigid. Likewise, the opening of the matrix by introduction of a gas allows it to be more easily morselized when it is frozen.

In one embodiment, the gas comprises normal air, $CO_2$, argon, nitrogen, or oxygen, or any combination thereof. In one embodiment, the gas comprises air. In one embodiment, the gas is a vapor. In one embodiment, the gas comprises an aerosolized drug, e.g., one or more steroids, antibiotics or antifungals. In one embodiment, the vapor component comprises a sterilization agent such as peracetic acid or hydrogen peroxide, or a carrier, such as phosphate buffered saline, lactose, glucose or liposome carriers, or a nebulizer type vapor, having various drugs or proteins including but not limited to one or more antibiotics, steroids, or anti-fungals, or proteins such as a cytokine or growth factor such as VEGF, FGF-2, EGF, PDGF, IGF, or HGF, or micro- or nano-particles comprising proteins, small molecules or drugs.

DETAILED DESCRIPTION

Figure 1:
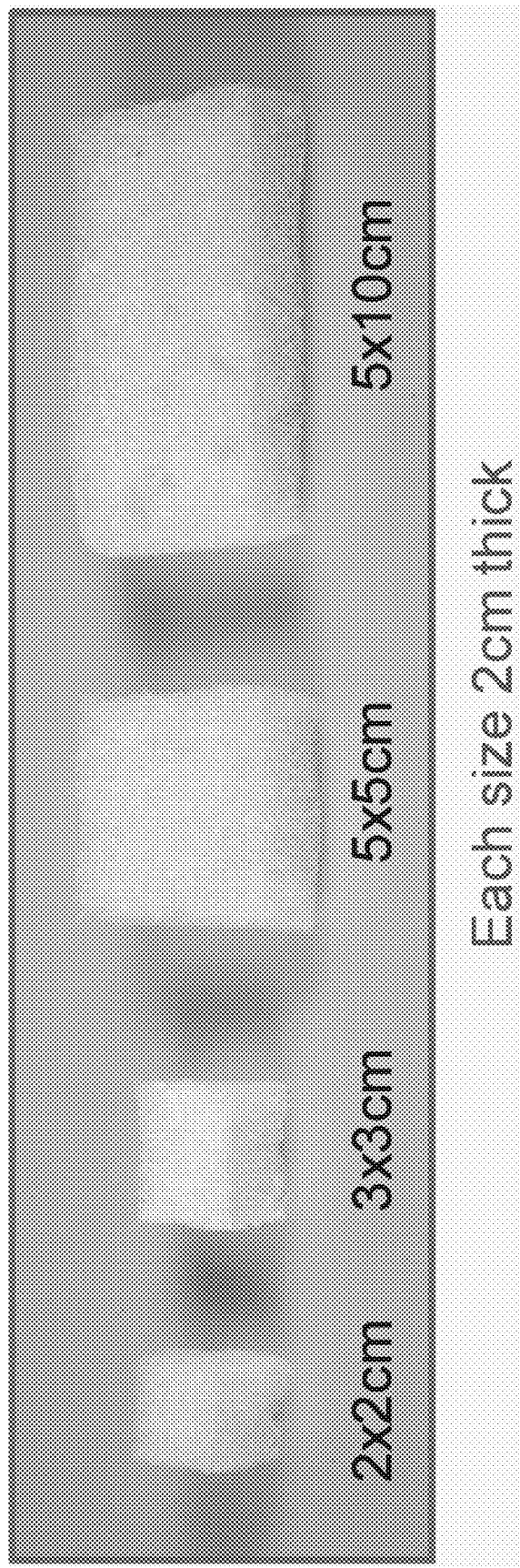
FIG. 1. Exemplary sizes of air dried decellularized extracellular matrix for wound care.
Figure 2A:
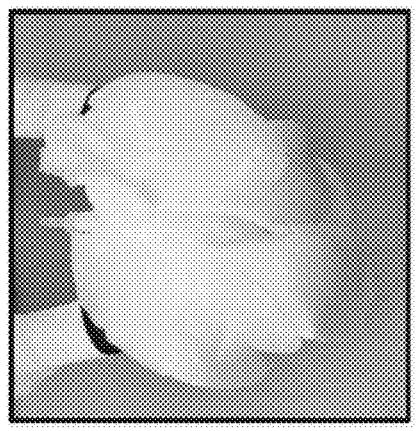
FIG. 2A-2D. Exemplary manufacturing steps. A) Porcine liver, decellularized. B) Dried decellularized porcine liver. C) Cut to size. D) Packaged, sealed and sterilized.
Figure 2B:
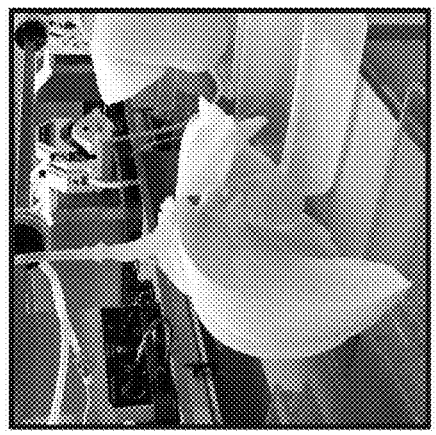
Figure 2C:
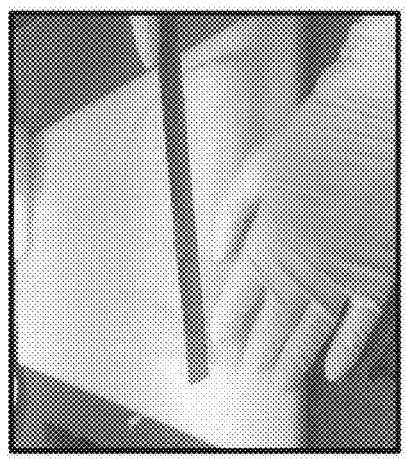
Figure 2D:
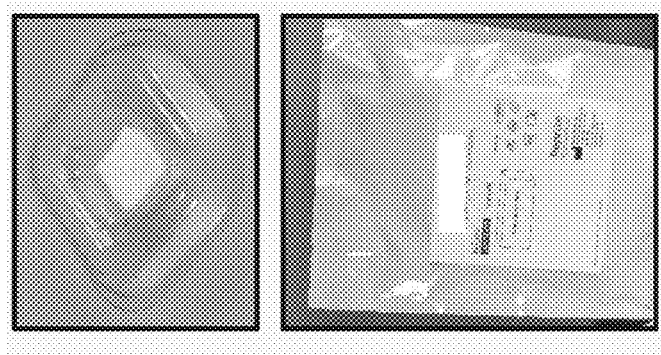
Figure 3:
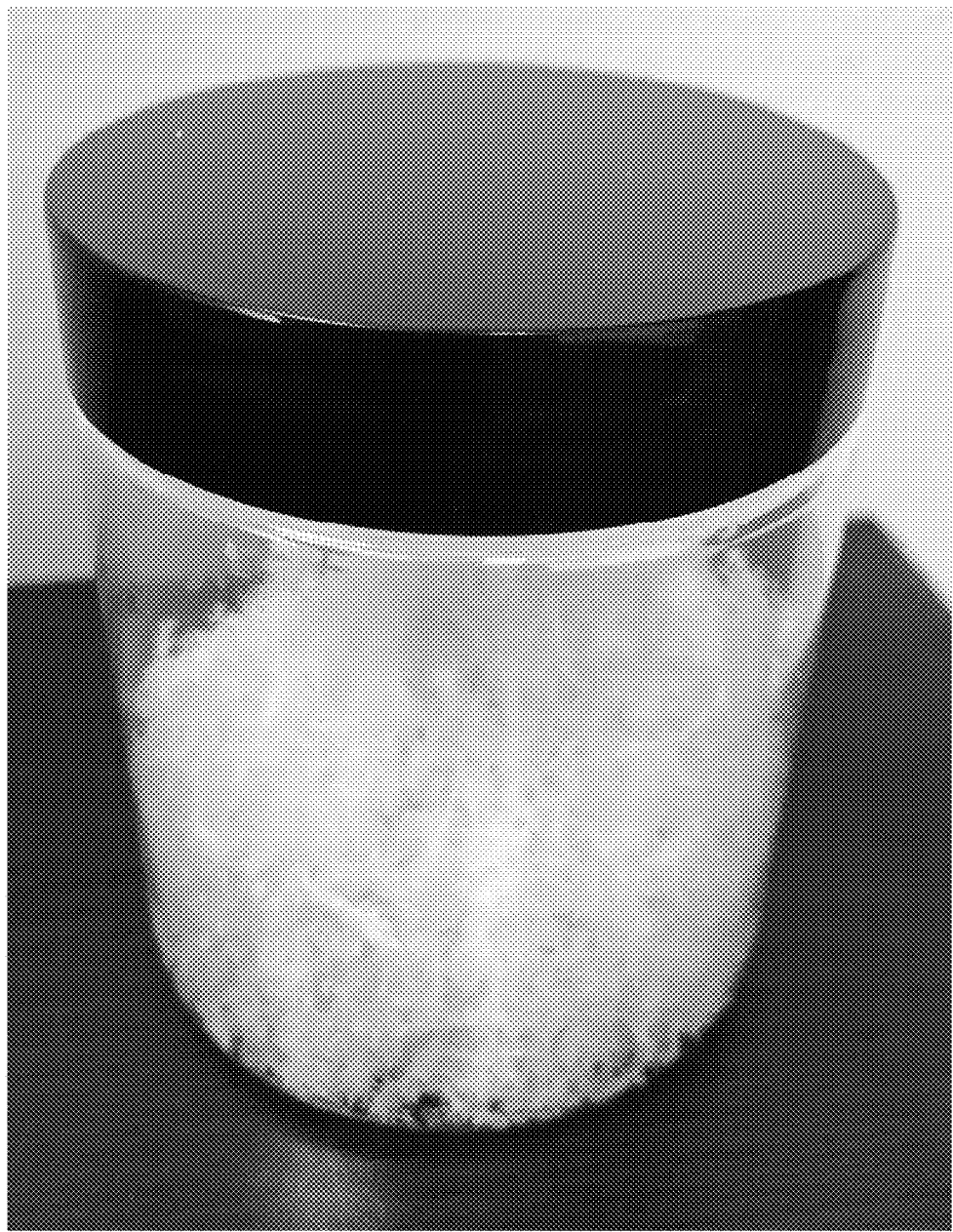
FIG. 3. An image of fibers produced by processing air dried decellularized extracellular matrix.
Figure 4:
FIG. 4. An image of fibers produced by processing air dried decellularized extracellular matrix.
Figure 5:
FIG. 5. An image of fibers produced by processing air dried decellularized extracellular matrix.

Decellularization results in an acellular tissue or organ that has extracellular matrix. The resulting space that was originally occupied by cells is occupied by the decellularization solution or whatever solution the tissue is in. In tissues and organs such as liver, lung, muscle, spleen and heart that contain a high ratio of cells compared to extracellular matrix, e.g., a ratio of 1:3 to 1:20 depending on the type of tissue, the original shape of the organ or tissue is reduced as compartments that once contained the cells collapse. While the original shape of the organ or tissue can be maintained if it is perfused under pressure, but once removed from that, the organ or tissue will deflate as the fluid slowly drains out. To create a three dimensional matrix that maintains the original shape, size or volume of the organ or tissue, a gas or a gas including particles or droplets (vapor) is introduced to at least one a vessel, duct or cavity of the decellularized organ or tissue to fill the void spaces resulting in a three dimensional matrix that can be cut, shaped and/or modeled for various uses without collapsing of the compartment(s) where cells used to reside.

Thus, the invention provides, in one embodiment, active access to the vascular network of a decellularized organ or tissue. This can be accomplished by cannulating, directly injecting into the ECM or use of a positive displacement device, and optionally sealing any main vein or artery belonging to the decellularized organ or tissue. In some embodiments, other vascular channels may be blocked off to create a more closed vascular system. In one embodiment, a pump, syringe, pressurized gas, canned gas and/or a canister containing a gas or a vapor comprising one or more proteins, small molecules, drugs or other agents, is used to actively introduce a gas or a vapor, including for example applying a vacuum outside the tissue to cause distribution of introduced gases and/or vapors, for instances at pump rates, e.g., about 10 to about 10,000 mL/min, e.g., about 3,000 mL/min to about 5,000 mL/min, about 100 mL/min to about 1,000 mL/minute, 1000 mL/min to 3,000 mL/min or 5,000 mL/min to 7,500 mL/min, and pressures from about 1 to about 200 mmHg, about 1 to about 50 mmHg, about 50 to 100 mmHg, about 100 to 150 mmHg or about 150 to 200 mmHg. In one embodiment, a gas or vapor may be introduced into the decellularized organ or tissue through tubing, cannulas, connectors, needles and/or syringes connected to a cannulated arterial or venous vessel. The gas or vapor is pumped at a determined rate, e.g., 2,000 mL/min to about 4,000 mL/min, until desired results are achieved, e.g., as determined visually or via physical measurements, for instance, filling to a defined volume or volumetric shape, increased surface tension and/or increased back pressure. The gas or vapor in the inflated organ or tissue becomes trapped in the cellular compartments and remains there.

The gas or vapor filled and dried decellularized organ or tissue matrix can be employed in various therapeutic applications including the use of the whole decellularized organ or tissue, or portions of the organ or tissue, useful as surgical fillers, surgical mesh, fillers for fistulas and other voids, e.g., wound beds or cavities, and to prepare portions, e.g., granular or morselized pieces, of the decellularized ECM of the organ or tissue. Morsels are about 0.5 mm to about 10 mm in diameter; granules are <about 0.5 mm in diameter. Morsal production may include grating the expanded ECM and then running the pieces through a series of strainers to achieve the desired size range of morsels. Granule production may include grinding the grated pieces down into smaller pieces and then running them through a series of even smaller strainers to achieve the desired granule size range.

In one embodiment, the gas inflated (expanded) and dried decellularized matrix is used as a shape retaining surgical filler. In one embodiment, the gas inflated decellularized matrix is used for the use in treatment of fistula. In one embodiment, the gas inflated decellularized matrix is subjected to e-beam sterilization, e.g., to set the protein conformation of the matrix thereby increasing the retention of its shape. In one embodiment, the gas used to inflate the decellularized matrix sterilizes the decellularized matrix. The inflation of the decellularized matrix allows for ease of cutting desired three-dimensional portions of the matrix, ease of cryodesiccating and/or morselizing the decellularized matrix for wound applications. In one embodiment, the decellularized matrix is inflated with a vapor, or after an initial inflation with a non-particle containing, non-droplet containing gas exposed to a vapor, having one or more drugs, e.g., one or more cytokines or growth factors to induce remodeling in vivo and/or to increase cellular engraftment when seeded with cells. In one embodiment, the decellularized matrix is inflated with a vapor containing one or more small molecules or proteins, or after an initial inflation with a non-particle containing, non-droplet containing gas exposed to a vapor, having one or more drugs, to be slowly released in-vivo acting as controlled delivery vehicle, carrier or device.

Exemplary Sources of Organs and Tissues for Decellularized ECM

A tissue is a group of cells with a common structure and function, e.g., epithelial tissue, connective tissue, muscle tissue (skeletal, cardiac, or smooth muscle), and nervous tissue, and includes a pliable sheet that covers or lines or connects organs. An organ is a collection of tissues (two or more) joined in structural unit to serve a common function. Organs include but are not limited to the brain, liver, pancreas, bone, spleen, heart, stomach, kidney, lungs, whole muscles, thymus, anus, and intestine. As used herein, an organ includes perfusable whole organs, or parts of an organ, or vascularized structures thereof, and a tissue includes any structures that contain vascularized tissues, e.g., a trachea.

In one embodiment, a portion of an organ or tissue or ECM thereof, is employed in the methods of the invention, e.g., an atrium or ventricle of a heart or interior structure of a pancreas including islets. In one embodiment, the portion is about 5 to about 10 mm in thickness. In one embodiment, the portion is about 70 to about 100 mm in thickness.

The ECM of an organ or tissue, or a vascularized portion thereof, may be obtained from any source including, without limitation, heart, liver, lungs, skeletal muscles, brain, pancreas, spleen, kidneys, uterus, eye, spinal cord, intestine, omentum, whole muscle, or bladder, or any portion thereof (e.g., an aortic valve, a mitral valve, a pulmonary valve, a tricuspid valve, a pulmonary vein, a pulmonary artery, coronary vasculature, septum, a right atrium, a left atrium, a right ventricle, or a left ventricle). A solid organ refers to an organ that has a "substantially closed" vasculature system. A "substantially closed" vasculature system with respect to an organ means that, upon perfusion with a liquid, the majority of the liquid is contained within the solid organ or runs through the native vascular structures and does not leak out of the solid organ, assuming the major vessels are cannulated, ligated, or otherwise restricted. Despite having a "substantially closed" vasculature system, many of the organs listed above have defined "entrance" and "exit" vessels which are useful for introducing and moving the liquid throughout the organ during perfusion. In addition, other types of vascularized organs or tissues such as, for example, all or portions of joints (e.g., knees, shoulders, or hips), anus, trachea, or spinal cord, can be perfusion decellularized. Further, avascular tissues such as, for example, cartilage or cornea, may be decellularized when part of larger vascularized structures such as a whole leg.

Perfusion decellularized matrices of organs with a substantially closed vascular system are useful because perfusion decellularization preserves the intact matrix and microenvironment, including an intact vascular and microvascular system, that vascular system, or ducts or other conduits, may be utilized to deliver nutrients and/or differentiation or maintenance factors. Nutrients and/or other growth factors may be delivered by other means, e.g., injection, or passive means, or a combination thereof.

Decellularization of Organs or Tissues

Decellularization generally includes the following steps: stabilization of the solid organ, e.g., a vascularized structure thereof, or tissue, decellularization of the solid organ or tissue, renaturation and/or neutralization of the solid organ or tissue, washing the solid organ, degradation of any DNA remaining on the organ, disinfection of the organ or tissue and homeostasis of the organ.

The initial step in decellularizing an organ's vascularized structure or tissue is to cannulate the organ or tissue. The vessels, ducts, and/or cavities of an organ or tissue may be cannulated using methods and materials known in the art.

Next, the cannulated organ vascularized structure or tissue is perfused with a cellular disruption medium. Perfusion through an organ can be multi-directional (e.g., antegrade and retrograde).

Langendorff perfusion of a heart is routine in the art, as is physiological perfusion (also known as four chamber working mode perfusion). See, for example, Dehnert, The Isolated Perfused Warm-Blooded Heart According to Langendorff, In Methods in Experimental Physiology and Pharmacology: Biological Measurement Techniques V. Biomesstechnik-Verlag March GmbH, West Germany, 1988.

Briefly, for Langendorff perfusion, the aorta is cannulated and attached to a reservoir containing physiological solution to allow the heart to function outside of the body for a specified duration of time. To achieve perfusion decellularization, the protocol has been modified to perfuse a cellular disruption medium delivered in a retrograde direction down the aorta either at a constant flow rate delivered, for example, by an infusion or roller pump or by a constant hydrostatic pressure pump. In both instances, the aortic valves are forced shut and the perfusion fluid is directed into the coronary ostia (thereby perfusing, via antegrade, the entire ventricular mass of the heart), which then drains into the right atrium via the coronary sinus. For working mode perfusion, a second cannula is connected to the left atrium and perfusion can be changed to retrograde.

In one embodiment, a physiological solution includes phosphate buffer saline (PBS). In one embodiment, the physiological solution is a physiologically compatible buffer supplemented with, e.g., nutritional supplements (for instance, glucose). For liver, the physiological solution may be Krebs-Henseleit buffer having 118 mM NaCl, 4.7 mM KCl, 1.2 mM $MgSO_4$, 1.2 mM $KH_2PO_4$, 26 mM $NaHCO_3$, 8 mM glucose, and 1.25 mM $CaCl_2$ supplemented with 2% BSA. The physiological solution may be Miami modified media-1 supplemented with or without prolactin or modified CMRL 1066 tissue culture media containing: 10% fetal bovine serum, 25 mM HEPES, 100 units/ml penicillin, and 100 µg/ml streptomycin, pH 7.4 with or without VEGF.

Methods are known in the art for perfusing other organ or tissues. By way of example, the following references describe the perfusion of lung, liver, kidney, brain, and limbs. Van Putte et al., *Ann. Thorac. Surg.*, 74(3):893 (2002); den Butter et al., *Transpl. Int.*, 8:466 (1995); Firth et al., *Clin. Sci. (Lond.)*, 77(6):657 (1989); Mazzetti et al., *Brain Res.*, 999(1):81 (2004); Wagner et al., *J. Artif. Organs*, 6(3):183 (2003).

One or more cellular disruption media may be used to decellularize an organ or tissue. A cellular disruption medium generally includes at least one detergent such as but not limited to SDS, PEG, CHAPS or Triton X. A cellular disruption medium can include water such that the medium is osmotically incompatible with the cells. Alternatively, a cellular disruption medium can include a buffer (e.g., PBS) for osmotic compatibility with the cells. Cellular disruption media also may include enzymes such as, without limitation, one or more collagenases, one or more dispases, one or more DNases, or a protease such as trypsin. In some instances, cellular disruption media also or alternatively may include inhibitors of one or more enzymes (e.g., protease inhibitors, nuclease inhibitors, and/or collegenase inhibitors).

In certain embodiments, a cannulated organ or tissue may be perfused sequentially with two different cellular disruption media. For example, the first cellular disruption medium may include an anionic detergent such as SDS and the second cellular disruption medium can include an ionic detergent such as Triton X. Following perfusion with at least one cellular disruption medium, a cannulated organ or tissue may be perfused, for example, with wash solutions and/or solutions containing one or more enzymes such as those disclosed herein.

Alternating the direction of perfusion (e.g., antegrade and retrograde) may assist in decellularizing the entire organ or tissue. Decellularization generally decellularizes the organ from the inside out, resulting in very little damage to the ECM. An organ or tissue may be decellularized at a suitable temperature between 4 and 40° C. Depending upon the size and weight of an organ or tissue and the particular detergent(s) and concentration of detergent(s) in the cellular disruption medium, an organ or tissue generally is perfused from about 0.05 hours to about 5 hours, per gram of solid organ or tissue (generally >50 grams), or about 2 hours to about 12 hours, per gram of solid organ or tissue for organs (generally <50 grams), with cellular disruption medium. Including washes, an organ may be perfused for up to about 0.75 hours to about 10 hours per gram of solid organ or tissue (generally >50 grams), or about 12 hours to about 72 hours, per gram of tissue (generally <50 grams). Decellularization time is dependent upon the vascular and cellular density of the organ or tissue with limited scaling for overall mass. Therefore, as general guidance the time ranges and masses above are provided. Perfusion generally is adjusted to physiologic conditions including pulsatile flow, rate and pressure.

A decellularized organ or tissue has the extracellular matrix (ECM) component of all or most regions of the organ or tissue, including ECM components of the vascular tree. ECM components can include any or all of the following: fibronectin, fibrillin, laminin, elastin, members of the collagen family (e.g., collagen I, III, and IV), ECM associated growth proteins including growth factors and cytokines, glycosaminoglycans, ground substance, reticular fibers and thrombospondin, which can remain organized as defined structures such as the basal lamina. Successful decellularization is defined as the absence of detectable myofilaments, endothelial cells, smooth muscle cells, and nuclei in histologic sections using standard histological staining procedures or removal of over 97% of detectable DNA as measured by fluorometric assay. Residual cell debris may be removed from the decellularized organ or tissue.

The morphology and the architecture of the ECM is maintained during and following the process of decellularization. "Morphology" as used herein refers to the overall shape of the organ, tissue or of the ECM, while "architecture" as used herein refers to the exterior surface, the interior surface, and the ECM therebetween.

The morphology and architecture of the ECM may be examined visually and/or histologically. For example, the basal lamina on the exterior surface of a solid organ or within the vasculature of an organ or tissue should not be removed or significantly damaged due to perfusion decellularization. In addition, the fibrils of the ECM should be similar to or significantly unchanged from that of an organ or tissue that has not been decellularized.

Exemplary Perfusion Decellularization of Heart

PEG Decellularization Protocol

Hearts are washed in 200 ml PBS containing 100 U/mL penicillin, 0.1 mg/ml Streptomycin, 0.25 □g/mL Amphotericin B, 1000 U of heparin, and 2 mg of Adenocard with no recirculation. Hearts are then decellularized with 35 ml polyethylene glycol (PEG; 1 g/mL) for up to 30 minutes with manual recirculation. The organ is then washed with 500 mL PBS for up to 24 hours using a pump for recirculation. The washing step is repeated at least twice for at least 24 hours each time. Hearts are exposed to 35 ml DNase I (70 U/mL) for at least 1 hour with manual recirculation. The organs are washed again with 500 ml PBS for at least 24 hours.

Triton X and Trypsin Decellularization Protocol

Hearts are washed in 200 ml PBS containing 100 U/mL Penicillin, 0.1 mg/mL Streptomycin, 0.25 □g/mL Amphotericin B, 1000 U of heparin, and 2 mg of Adenocard for at least about 20 minutes with no recirculation. Hearts are then decellularized with 0.05% Trypsin for 30 minutes followed by perfusion with 500 mL PBS containing 5% Triton-X and 0.1% ammonium-hydroxide for about 6 hours. Hearts are perfused with deionized water for about 1 hour, and then perfused with PBS for 12 hours. Hearts are then washed 3 times for 24 hours each time in 500 mL PBS using a pump for recirculation. The hearts are perfused with 35 ml DNase I (70 U/mL) for 1 hour with manual recirculation and washed twice in 500 mL PBS for at least about 24 hours each time using a pump for recirculation.

1% SDS Decellularization Protocol

Hearts are washed in 200 mL PBS containing 100 U/mL Penicillin, 0.1 mg/mL Streptomycin, 0.25 □g/mL Amphotericin B, 1000 U of heparin, and 2 mg of Adenocard for at least about 20 minutes with no recirculation. The hearts are decellularized with 500 mL water containing 1% SDS for at least about 6 hours using a pump for recirculation. The hearts are then washed with deionized water for about 1 hour and washed with PBS for about 12 hours. The hearts are washed three times with 500 mL PBS for at least about 24 hours each time using a pump for recirculation. The heart is then perfused with 35 ml DNase I (70 U/mL) for about 1 hour using manual recirculation and washed three times with 500 mL PBS for at least about 24 hours each time using a pump for recirculation.

Triton X Decellularization Protocol

Hearts are washed with 200 mL PBS containing 100 U/mL Penicillin, 0.1 mg/ml Streptomycin, 0.25 □g/mL Amphotericin B, 1000 U of heparin, and 2 mg of Adenocard (adenosine) for at least about 20 minutes with no recirculation. Hearts are then decellularized with 500 mL water containing 5% Triton X and 0.1% ammonium hydroxide for at least 6 hours using a pump for recirculation. Hearts are then perfused with deionized water for about 1 hour and then with PBS for about 12 hours. Hearts are washed by perfusing with 500 mL PBS 3 times for at least 24 hours each time using a pump for recirculation. Hearts are then perfused with 35 ml DNase I (70 U/mL) for about 1 hour using manual recirculation [,] and washed three times in 500 ml PBS for about 24 hours each time.

Hearts may be perfused at a coronary perfusion pressure of 60 cm $H_2O$. Although not required, the hearts may be mounted in a decellularization chamber and completely submerged and perfused with PBS containing antibiotics for 72 hours in recirculation mode at a continuous flow of 5 mL/minute to wash out as many cellular components and detergent as possible.

Detection of Decellularization

Successful decellularization may be measured by the lack of nucleic acid in histologic sections. Successful preservation of vascular structures may be assessed by perfusion with 2% Evans Blue prior to embedding tissue sections. Highly efficient decellularization may be observed when an organ is first perfused antegradely with an ionic detergent (1% sodium-dodecyl-sulfate (SDS), approximately 0.03 M) dissolved in deionized $H_2O$ at a constant coronary perfusion pressure and then perfused antegradely with a non-ionic detergent (1% Triton X-100) to remove the SDS and presumably to renature the extracellular matrix (ECM) proteins. Intermittently, the organ may be perfused retrogradely with phosphate buffered solution to clear obstructed capillaries and small vessels.

To demonstrate intact vascular structures following decellularization, a decellularized organ may be stained via Langendorff perfusion with Evans Blue to stain vascular basement membrane and quantify macro- and micro-vascular density.

A physiological buffer may be employed before or after decellularization, and before drying, generally at physiological pH. In one embodiment, the physiological buffer includes but is not limited to phosphate buffer saline (PBS) or culture media solutions e.g., DMEMF/12, buffers along with nutritional supplements, e.g., glucose, including but not limited to Modified Krebs-Henseleit buffer of the following composition was prepared (in mM): 118 NaCl, 4.7 KCl, 1.2 $MgSO_4$, 1.2 $KH_2PO_4$, 25 $NaHCO_3$, 11 glucose, 1.75 $CaCl_2$, and 2.0 pyruvate and 5 U/L insulin or Krebs buffer containing (in mM) 118 NaCl, 4.7 KCl, 25 $NaHCO_3$, 1.2 $MgSO_4$, $1.2_{KH2PO4}$, 2 CaCl2) gassed with 95% O2, 5% CO2; or glucose (e.g., 11 mM) or glucose in combination with 1 or 1.2 mM palmitate, KPS-1 Kidney Perfusion Solution, or Krebs-Henseleit buffer containing 118 mM NaCl, 4.7 mM KCl, 1.2 mM $MgSO_4$, 1.2 mM $KH_2PO_4$, 26 mM $NaHCO_3$, 8 mM glucose, and 1.25 mM $CaCl_2$ supplemented with 2% BSA, KODMEM medium (Knockout Dulbecco's Modified Eagle's Medium), DMEM, Ham's F12 medium, FBS (fetal bovine serum), FGF2 (fibroblast growth factor 2), KSR or hLIF (human leukemia inhibitory factor).

Controlled System for Decellularizing An Organ or Tissue

A system for decellularizing an organ or tissue generally includes at least one cannulation device for cannulating an organ or tissue, a perfusion apparatus for perfusing the organ or tissue through the cannula(s), and optionally a means (e.g., a containment system) to maintain a sterile environment for the organ or tissue. Cannulation and perfusion are well-known techniques in the art. A cannulation device generally includes size-appropriate hollow tubing for introducing into a vessel, duct, and/or cavity of an organ or tissue. Typically, one or more vessels, ducts, and/or cavities are cannulated in an organ. A perfusion apparatus can include a holding container for the liquid (e.g., a cellular disruption medium) and a mechanism for moving the liquid through the organ (e.g., a pump, air pressure, gravity) via the one or more cannulae. The sterility of an organ or tissue during decellularization can be maintained using a variety of techniques known in the art such as controlling and filtering the air flow and/or perfusing with, for example, antibiotics, anti-fungals or other anti-microbials to prevent the growth of unwanted microorganisms.

A system to decellularize organ or tissues as described herein can possess the ability to monitor certain perfusion characteristics (e.g., pressure, volume, flow pattern, temperature, gases, pH), mechanical forces (e.g., ventricular wall motion and stress), and electrical stimulation (e.g., pacing). As the coronary vascular bed changes over the course of decellularization (e.g., vascular resistance, volume), a pressure-regulated perfusion apparatus is advantageous to avoid large fluctuations. The effectiveness of perfusion can be evaluated in the effluent and in tissue sections. Perfusion volume, flow pattern, temperature, partial $O_2$ and $CO_2$ pressures and pH can be monitored using standard methods.

Sensors can be used to monitor the system (e.g., bioreactor) and/or the organ or tissue. Sonomicromentry, micromanometry, and/or conductance measurements can be used to acquire pressure-volume or preload recruitable stroke work information relative to myocardial wall motion and performance. For example, sensors can be used to monitor the pressure of a liquid moving through a cannulated organ or tissue; the ambient temperature in the system and/or the temperature of the organ or tissue; the pH and/or the rate of flow of a liquid moving through the cannulated organ or tissue. In addition to having sensors for monitoring such features, a system for decellularizing an organ or tissue also can include means for maintaining or adjusting such features. Means for maintaining or adjusting such features can include components such as a thermometer, a thermostat, electrodes, pressure sensors, overflow valves, valves for changing the rate of flow of a liquid, valves for opening and closing fluid connections to solutions used for changing the pH of a solution, a balloon, an external pacemaker, and/or a compliance chamber. To help ensure stable conditions (e.g., temperature), the chambers, reservoirs and tubings can be water-jacketed.

A system may be controlled by a computer-readable storage medium in combination with a programmable processor (e.g., a computer-readable storage medium as used herein has instructions stored thereon for causing a programmable processor to perform particular steps). For example, such a storage medium, in combination with a programmable processor, may receive and process information from one or more of the sensors. Such a storage medium in conjunction with a programmable processor also can transmit information and instructions back to the bioreactor and/or the organ or tissue.

In one embodiment, the weight of an organ or tissue may be entered into a computer-readable storage medium as described herein, which, in combination with a programmable processor, can calculate exposure times and perfusion pressures for that particular organ or tissue. Such a storage medium may record preload and afterload (the pressure before and after perfusion, respectively) and the rate of flow. In this embodiment, for example, a computer-readable storage medium in combination with a programmable processor can adjust the perfusion pressure, the direction of perfusion, and/or the type of perfusion solution via one or more pumps and/or valve controls.

EXEMPLARY EMBODIMENTS

An inflated and suspension dried decellularized extracellular matrix of a mammalian organ or tissue, or a vascularized portion thereof, is provided, wherein said decellularized extracellular matrix of the mammalian organ or tissue or the portion thereof comprises a decellularized vascular tree, duct or cavity, wherein when fluid is introduced to one entry point in said vascular tree of said decellularized extracellular matrix, said fluid is retained in the vascular tree so that the fluid exits through a different point in the vascular tree. In one embodiment, the mammalian organ is a heart, a kidney, a liver, spleen, pancreas, bladder, skeletal muscle, small bowel, large bowel, stomach, bone, brain, or a lung. In one embodiment, the vascularized portion is a portion of a mammalian heart, a kidney, a liver, spleen, pancreas, bladder, skeletal muscle, small bowel, large bowel, stomach, bone, brain, or a lung. In one embodiment, the inflated and suspension dried decellularized extracellular matrix is inflated and dried with air, oxygen or nitrogen. In one embodiment, the inflated and suspension dried decellularized extracellular matrix has an exterior surface or portion thereof. In one embodiment, the inflated and suspension dried decellularized extracellular matrix does not have an exterior surface or portion thereof. In one embodiment, the inflated and suspension dried decellularized extracellular matrix of has a thickness of about 1 cm to 2 cm, 1.5 cm to 2.5 cm or 2 cm to 3 cm. In one embodiment, the inflated and suspension dried decellularized extracellular matrix has and retains a height that is increased by at least 25% relative to a corresponding uninflated and/or nonsuspension dried decellularized extracellular matrix of the mammalian organ or tissue, or portion thereof. In one embodiment, the inflated and suspension dried decellularized extracellular matrix is about 2 cm (L)×2 cm (W)×2 cm (T), 3 cm (L)×3 cm (W)×2 cm (T), 5 cm (L)×5 cm (W)×2 cm (T), 10 cm (L)×5 cm (W)×2 cm (T) or 10 cm (L)×10 cm (W)×2 cm (T). In one embodiment, the decellularized organ or vascularized tissue is from a pig, bovine, sheep, canine or human. In one embodiment, the decellularized organ is a pig liver.

Also provided is a method of inflating and suspension drying a decellularized extracellular matrix of a mammalian organ or tissue, or a vascularized portion thereof, comprising: providing a suspended decellularized extracellular matrix of a mammalian organ or tissue, or portion thereof, wherein said extracellular matrix of said organ optionally comprises an exterior surface, wherein said extracellular matrix of said organ or tissue, or portion thereof, comprises a vascular tree, wherein said decellularized extracellular matrix of said organ or tissue or portion thereof retains a majority of fluid introduced to the decellularized extracellular matrix vascular tree, and wherein said organ has a substantially closed vasculature bed; cannulating said organ or tissue, or portion thereof, at one or more vessels, cavities and/or ducts, thereby producing a cannulated organ or portion thereof or a cannulated tissue or portion thereof; and introducing a gas into said one or more vessels, cavities or ducts of said cannulated organ or portion thereof, for at least four hours so as to provide an inflated and suspension dried extracellular matrix. In one embodiment, the gas is introduced for up to 96 hours. In one embodiment, the gas is introduced for up to 72 hours. In one embodiment, the gas is introduced at a maximum rate of 4000 mL/min. In one embodiment, the gas is introduced at least 100 mL/min. In one embodiment, the inflated decellularized extracellular matrix has and retains a height that is increased by at least 25% relative to a corresponding uninflated decellularized extracellular matrix of the mammalian organ or tissue, or portion thereof. In one embodiment, the gas comprises air, nitrogen or oxygen. In one embodiment, the mammal is a human, non-human primate, bovine, porcine, canine, feline, caprine, ovine, or rodent. In one embodiment, the method includes separating the inflated and suspension dried extracellular matrix into one or more portions greater than about 0.5 cm (L)×0.5 cm (W)×0.5 cm (T). In one embodiment, the method includes removing the exterior surface. In one embodiment, the method includes sterilizing the inflated and suspension dried decellularized extracellular matrix or a portion thereof. In one embodiment, the mammalian organ is a heart, a kidney, a liver, spleen, pancreas, bladder, skeletal muscle, small bowel, large bowel, stomach, bone, brain, or a lung.

Further provided is a portion of an inflated and suspension dried decellularized extracellular matrix of a mammalian organ or tissue, produced by the method or a product comprising layers of a portion of an inflated and suspension dried decellularized extracellular matrix of a mammalian organ or tissue, produced by the method.

In one embodiment, a method to augment a void or treat a wound in a body cavity, or to treat a topical wound, of a mammal, is provided comprising administering to the void or the wound the portion of the extracellular matrix or the product. In one embodiment, the administration is to a fistula. In one embodiment, the administration is to a hernia.

In one embodiment, a composition is provided comprising one or more portions of decellularized extracellular matrix of a mammalian organ or tissue, comprising particles or fibers comprising a length from about 0.05 mm to about 25 mm. In one embodiment, the composition is dry. In one embodiment, the composition further comprises a pharmaceutically acceptable carrier. In one embodiment, the carrier is an aqueous carrier. In one embodiment, the particles or fibers comprise a length of about 0.1 mm to about 20 mm. In one embodiment, at least 50%, 60%, 70%, 80%, 90% 95% or 99% of the particles or fibers in the composition have a length of about 0.05 mm to about 25 mm.

The invention will be described by the following non-limiting example.

EXAMPLE

In one embodiment, the disclosure provides for methods to dry and/or inflate decellularized extracellular matrix obtained from a mammalian organ, tissue or portion thereof, e.g., >1 cm$^3$. In one embodiment, a product of the method is divided into portions, e.g., cut into 2 cm×2 cm portions, thereby providing a three-dimensional (e.g., 2 cm thick) collagen matrix for wound care which may be useful to replace volume in a wound area including a surgically created void. In one embodiment, the decellularized extracellular matrix is a decellularized porcine liver. In one embodiment, the product may be used to cover a wound, e.g., on the skin, not replace volume. In one embodiment, the product is greater than 1 to 3 mm in thickness. In one embodiment, the product is 1 cm to 3 cm, e.g., about 2 cm, thick with a length and width of, for example, 2 cm×2 cm, 3 cm×3 cm, 5 cm×5 cm or 5 cm×10 cm (FIG. 1). In one embodiment, the product is 2 cm×2 cm×2 cm to 10 cm×5 cm×2 cm. In one embodiment, thicknesses of less than 2.5 cm are envisioned, e.g., 0.5 cm to 1.5 cm, 1.5 cm to 2.5 cm, or 1.75 cm to 2.25 cm. In one embodiment, portions are layered, e.g., to prepare thicknesses of greater than 2 cm.

In one embodiment, the portion is not compressed. In one embodiment, the portion is packaged dry. In one embodiment, the portion is packaged wet, e.g., in the presence of a physiologically compatible aqueous solution.

In one embodiment, the gas used for inflation is ambient air. In one embodiment, the gas used for inflation may comprise a drug, aerosolized drug, or proteins such as cytokine or growth factors. In one embodiment, the portion of inflated decellularized matrix has been granularized or morselized. In one embodiment, the portion of inflated decellularized matrix has been milled, e.g., to a product having a range of sizes from, in one embodiment, about 0.1 mm to about 20 mm in length. In one embodiment, to augment a void or treat a wound in the body, the portion of inflated decellularized matrix has been cryodesiccated. In one embodiment the portion is used to treat a fistula.

In one embodiment, the passage of a gas through the decellularized extracellular matrix both dries and inflates the matrix. In one embodiment, the inflation occurs over about 2 to about 120 hours, e.g., about 4 hours to about 96 hours. In one embodiment, the drying occurs over about 2 to about 120 hours, e.g., about 4 hours to about 96 hours. In one embodiment, inflation and drying occurs over about 65 to about 85 hours, e.g., 72 hours. Inflation and/or drying time affects the mechanical properties and density of the final material. In one embodiment, the decellularized extracellular matrix is suspended (see FIG. 2) and air-dried, thereby allowing for free expansion in all directions, ensuring homogenous drying and/or maximizing manufacturing yields.

In one embodiment, the capsule or exterior surface of the organ, e.g., a liver, is removed either before or after inflation and drying or after inflation and drying and either before or after providing portions. In one embodiment, the portion is sterilized, e.g., using E-beam irradiation, for example at a dose of 25-35 kGy.

In one embodiment, the portion is employed to augment a void or treat a wound in a body cavity. In one embodiment, the portion is employed to treat a topical wound.

In one embodiment, the decellularized extracellular matrix of an organ or a portion thereof is subjected to cross-linking, e.g., using vapor crosslinking with an aldehyde.

In one embodiment, either prior to inflation and/or drying or after inflation and/or drying, e.g., after providing portions, the decellularized extracellular matrix is contacted with one or more of an antimicrobial, an antibiotic, an anti-inflammatory drug (such as NSAIDs), and/or an analgesic.

In one embodiment, inflation and drying are conducted simultaneously. In one embodiment, air is pumped into a decellularized liver which both inflates and dries the liver throughout. In one embodiment, following decellularization, an organ, e.g., porcine liver, is inflated through the native vasculature. In one embodiment, air is pumped through the organ, e.g., liver, by way of pumping ambient air through a cannulated vessel, e.g., of a liver. In one embodiment, during the inflation and/or drying times (e.g., from about 4 to 96 hours), air is continuously being pumped through the decellularized organ, e.g., liver, during this period. In one embodiment, air is pumped through the organ, e.g., liver, at a maximum rate of 4000 mL/min. In one embodiment, air is pumped through the organ, e.g., liver, at a rate of at least 100 mL/min. In one embodiment, air is pumped through the organ, e.g., liver, at a rate of at least 200 mL/min.

In one embodiment, after suspension drying resulting from inflation with and flow of a gas through the decellularized extracellular matrix of a mammalian organ or tissue, or a vascularized portion thereof, the resulting product has a thickness that is greater than or about 2 cm or 3 cm. In one embodiment, a product with a thickness that is greater than or about 2 cm or 3 cm can be portioned, e.g., into a product with a thickness that is less than about 3 cm, e.g., a product with a thickness of about 1 cm to 1.5 cm, about 1.5 cm to 2 cm or about 1.75 cm to about 2.25 cm, e.g., about 2 cm.

In one embodiment, after suspension drying resulting from inflation with and flow of a gas through the decellularized extracellular matrix of a mammalian organ or tissue, or a vascularized portion thereof, the product may be compressed, e.g., using one or a series of mechanical presses.

In one embodiment, prior to suspension drying, the decellularized extracellular matrix of a mammalian organ or tissue, or a vascularized portion thereof, may be compressed, e.g., using one or a series of mechanical presses.

In one embodiment, the exterior surface may be removed prior to suspension drying.

In one embodiment, the exterior surface may be removed after suspension drying.

In one embodiment, the flow of the gas is controlled by a pump and a computer program in response to an in-line pressure transducer providing real time pressures.

In one embodiment, inflation/drying times are about 4 hrs up to about 96 hrs, e.g., about 72 hrs.

In one embodiment, following decellularization, porcine livers are inflated through the native vasculature of the liver, e.g., air is pumped through the liver by way of pumping ambient air through a cannulated vessel of the liver. In one embodiment, ambient air is pumped through a decellularized organ, e.g., a liver, at a maximum rate of 4000 mL/min.

Suspension of the liver during inflation allows the liver to inflate and therefore dry uniformly. This homogeneity throughout the material allows for maximized manufacturing yields, uniform material density, and uniform moisture content. The resulting uniform material is very porous in all directions (all surfaces) which may assist in efficient healing, integration, and remodeling when used for its clinical purpose.

In one embodiment, the particles/fibers vary in size, e.g., from about 0.05 mm to about 25 mm or about 0.1 mm to about 20 mm. In one embodiment, at least 50%, 60%, 70%, 80%, 90% 95% or 99% of the particles or fibers in the composition have a length of about 0.05 mm to about 25 mm, e.g., at least about 70% to 80% of the particles or fibers in the composition have a length of about 0.05 mm to about 25 mm.

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method for manufacturing a collagen matrix, comprising:
    obtaining a vascularized mammalian organ or tissue or a vascularized portion thereof;
    decellularizing the organ or tissue or portion thereof via perfusion decellularization through vascular pathways of the organ or tissue or portion thereof; and
    suspension drying the decellularized organ or tissue or portion thereof, including forcing a gas through the vascular pathways at a flow rate of up to about 4,000 mL/minute for about 2 to about 120 hours, such that the organ or tissue or portion thereof expands three-dimensionally relative to its non-inflated configuration and forms a matrix scaffold comprising a plurality of pores,
    wherein suspension drying the decellularized organ or tissue or portion thereof results in a matrix scaffold having a moisture content of no more than 8%.

2. The method of claim 1, wherein suspension drying the decellularized organ or tissue or portion thereof includes controlling the flow rate of the gas through the vascular pathways in response to a monitored in-line pressure.

3. The method of claim 2, wherein the flow rate of the gas through the vascular pathways is about 2,000 mL/minute to about 4,000 mL/minute.

4. The method of claim 1, wherein suspension drying the decellularized organ or tissue or portion thereof results in a matrix scaffold having a substantially uniform density.

5. The method of claim 1, wherein suspension drying the decellularized organ or tissue or portion thereof results in a matrix scaffold having a substantially uniform moisture content.

6. The method of claim 1, wherein forcing the gas through the vascular pathways such that the organ or tissue or portion thereof expands three-dimensionally relative to its non-inflated configuration includes increasing a size or volume of the organ or tissue or portion thereof about 25% to about 125% relative to its non-inflated configuration.

7. The method of claim 6, wherein the expanded organ or tissue or portion thereof retains a general shape of its non-inflated configuration.

8. The method of claim 1, wherein forcing the gas through the vascular pathways includes trapping gas in spaces occupied by cells prior to decellularization.

9. The method of claim 1, wherein the collagen matrix retains a morphology of the organ or tissue or portion thereof prior to decellularization.

10. The method of claim 1, further comprising processing the matrix scaffold into a plurality of particles or fibers having a length from about 0.05 millimeters to about 25 millimeters.

11. The method of claim 1, further comprising processing the matrix scaffold into a plurality of particles or fibers having a diameter less than about 0.5 millimeters.

12. The method of claim 1, further comprising processing the matrix scaffold into a plurality of particles or fibers having a diameter from about 0.5 millimeters to about 10 millimeters.

13. The method of claim 1, further comprising removing an exterior surface of the decellularized organ or tissue or portion thereof prior to suspension drying.

14. The method of claim 1, further comprising removing an exterior surface of the decellularized organ or tissue or portion thereof after suspension drying.

15. The method of claim 1, further comprising perfusing an antimicrobial agent into the vascular pathways of the organ or tissue or portion thereof following its decellularization.

16. The method of claim 1, further comprising perfusing one or more cytokines or growth factors into the vascular pathways of the organ or tissue or portion thereof following its decellularization.

17. The method of claim 1, further comprising perfusing one or more steroids, antibiotics, or antifungals into the vascular pathways of the organ or tissue or portion thereof following its decellularization.

18. The method of claim 1, further comprising cross-linking the organ or tissue or portion thereof following its decellularization.

* * * * *